US011534225B2

(12) United States Patent
Bluvshtein et al.

(10) Patent No.: US 11,534,225 B2
(45) Date of Patent: Dec. 27, 2022

(54) CONTROL AND INVERTER DESIGN TOPOLOGIES FOR ELECTRONIC MEDICAL DEVICES

(71) Applicant: MINNETRONIX, INC., Saint Paul, MN (US)

(72) Inventors: Vlad Bluvshtein, Plymouth, MN (US); Lori Lucke, Rosemount, MN (US)

(73) Assignee: MINNETRONIX, INC., St. Paul, MN (US)

(*) Notice: Subject to any disclaimer, the term of this patent is extended or adjusted under 35 U.S.C. 154(b) by 799 days.

(21) Appl. No.: 15/915,795

(22) Filed: Mar. 8, 2018

(65) Prior Publication Data
US 2018/0256242 A1    Sep. 13, 2018

Related U.S. Application Data

(60) Provisional application No. 62/470,007, filed on Mar. 10, 2017.

(51) Int. Cl.
*A61B 18/12*     (2006.01)
*H02M 7/5387*    (2007.01)
(Continued)

(52) U.S. Cl.
CPC ..... *A61B 18/1206* (2013.01); *H02M 7/53871* (2013.01); *H02M 7/53873* (2013.01);
(Continued)

(58) Field of Classification Search
CPC ............ A61B 18/1206; A61B 18/1233; A61B 2018/00577; A61B 2018/00601;
(Continued)

(56) References Cited

U.S. PATENT DOCUMENTS 4,092,986 A * 6/1978 Schneiderman ... A61B 18/1206
330/107
5,371,668 A   12/1994 Gurwicz et al.
(Continued)

FOREIGN PATENT DOCUMENTS

EP    2863533 A2    4/2015
JP    2014-180577   9/2014
JP    2014-183612   9/2014

OTHER PUBLICATIONS

International Search Report and Written Opinion of the International Searching Authority for International Patent Application No. PCT/US2018/021537, dated May 24, 2018 (13 pages).
Extended European Search Report received for European Patent Application No. 18764674.0, dated Nov. 24, 2020, 8 pages.

*Primary Examiner* — Eun Hwa Kim
*Assistant Examiner* — Catherine Premraj
(74) *Attorney, Agent, or Firm* — Seager, Tufte & Wickhem LLP

(57) ABSTRACT

Examples described herein may include medical devices and electrosurgical generators with resonant isolated transformers to perform filtering and gain functions. An example electrosurgical generator includes a radio frequency (RF) inverter stage configured to receive an input signal and, in response to control feedback signals, to provide an output signal that provides power to a load. The RF inverter stage includes a resonant isolated transformer configured to receive the input signal and to provide gain and filtering adjustments to the input signal to provide the output signal.

24 Claims, 12 Drawing Sheets

(51) Int. Cl.
*H02M 1/12* (2006.01)
*A61B 18/00* (2006.01)
*H02M 7/48* (2007.01)

(52) U.S. Cl.
CPC . *A61B 18/1233* (2013.01); *A61B 2018/00577* (2013.01); *A61B 2018/00601* (2013.01); *A61B 2018/00642* (2013.01); *A61B 2018/00648* (2013.01); *A61B 2018/00779* (2013.01); *A61B 2018/00791* (2013.01); *A61B 2018/00827* (2013.01); *A61B 2018/00892* (2013.01); *A61B 2018/1266* (2013.01); *A61B 2018/1286* (2013.01); *H02M 1/126* (2013.01); *H02M 7/4815* (2021.05); *Y02B 70/10* (2013.01)

(58) Field of Classification Search
CPC .......... A61B 2018/00642; A61B 2018/00648; A61B 2018/00779; A61B 2018/00791; A61B 2018/00827; A61B 2018/00892; A61B 2018/1266; A61B 2018/1286; H02M 7/53871; H02M 7/53873; H02M 1/126; H02M 2007/4815; Y02B 70/10
See application file for complete search history.

(56) References Cited

U.S. PATENT DOCUMENTS

| | | | |
|---|---|---|---|
| 6,582,427 B1* | 6/2003 | Goble | A61B 18/042 606/34 |
| 9,504,512 B2* | 11/2016 | Poulsen | A61B 18/14 |
| 2005/0281059 A1* | 12/2005 | Yasumura | H02M 1/4241 363/16 |
| 2006/0161148 A1 | 7/2006 | Behnke | |
| 2013/0066311 A1* | 3/2013 | Smith | A61B 18/1233 606/33 |
| 2014/0005667 A1* | 1/2014 | Stulen | A61B 34/30 606/45 |
| 2014/0276749 A1* | 9/2014 | Johnson | A61B 18/18 606/33 |
| 2014/0276754 A1* | 9/2014 | Gilbert | A61B 18/18 606/33 |
| 2015/0032096 A1* | 1/2015 | Johnson | A61B 18/18 606/34 |
| 2016/0113840 A1* | 4/2016 | Crunick | A61H 23/0218 601/95 |
| 2016/0217901 A1* | 7/2016 | Klinkowstein | H01F 19/00 |
| 2016/0254703 A1* | 9/2016 | Hansen | A61B 5/0031 307/104 |

* cited by examiner

CONTROL AND INVERTER DESIGN TOPOLOGIES FOR ELECTRONIC MEDICAL DEVICES

CROSS-REFERENCE TO RELATED APPLICATION

This application claims benefit under 35 U.S.C. § 119 of the earlier filing date of U.S. Provisional Application No. 62/470,007, filed Mar. 10, 2017, entitled "Control and Inverter Design Topologies for Electronic Medical Devices," which is hereby incorporated by reference in its entirety as if fully set forth herein.

BACKGROUND

Electrosurgery is a process of delivering high frequency electrical current to biological tissue to achieve medically relevant thermal effects. Tissue thermal effects depend on final temperature of the tissue and how fast the tissue was heated. Tissue temperature and temperature change rate can be monitored and controlled directly or inferred from tissue impedance. Electrical surgical units (ESUs) may be used to perform electrosurgery, but there are limitations in terms of response times and accuracy, which can sometimes lead to collateral tissue damage during a procedure.

DETAILED DESCRIPTION

The design considerations of ESUs may generally include at least response times and accuracy, adaptability to different therapies, size, complexity, safety, and cost. This disclosure proposes three general ideas to improve ESUs considering these design considerations.

Figure 1:
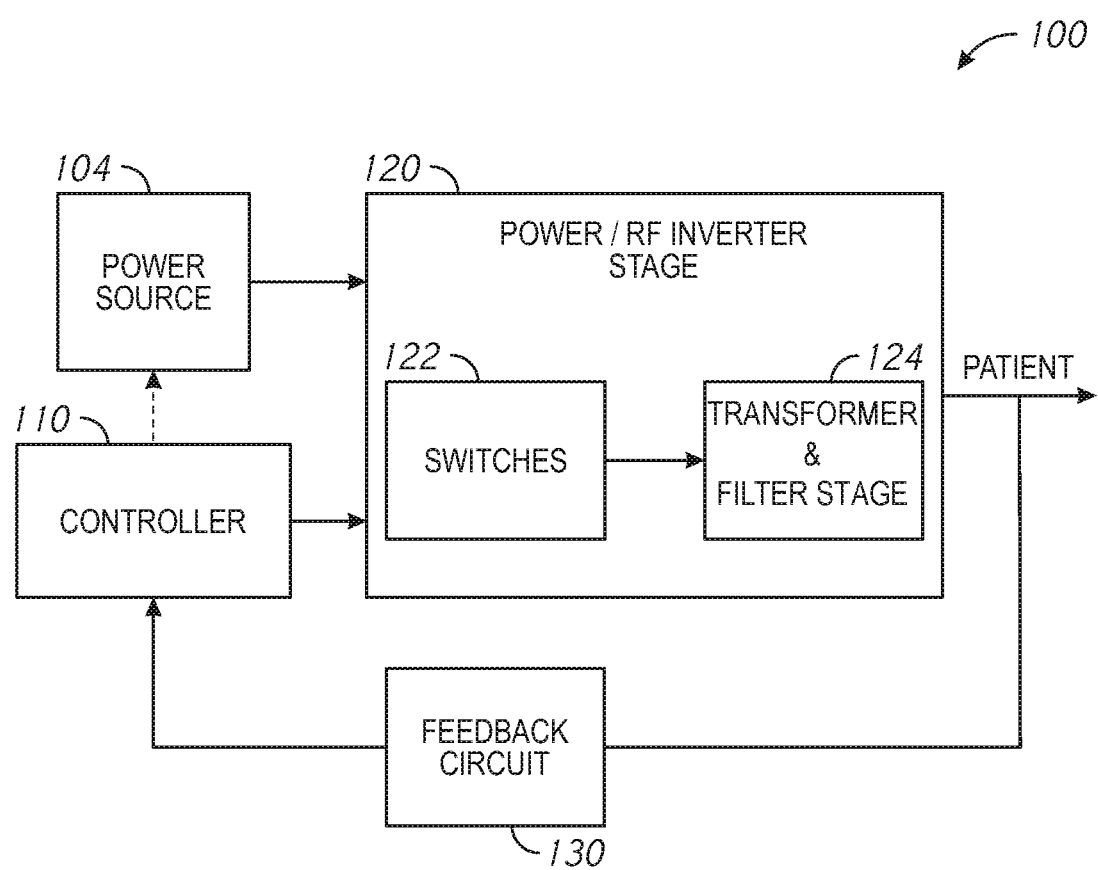
FIG. 1 is a block diagram of an example medical device according to embodiments of the disclosure.

FIG. 1 depicts an example medical device 100 according to an embodiment of the disclosure. The term medical device as used in this disclosure may reference any medical device concerned with controlling power/voltage/current/temperature to perform a procedure or therapy on a patient, including, but not limited to an ESU, a gas-based electrosurgical unit (for example, an argon gas based coagulation unit), RF ultrasound unit, and plasma units. The medical device 100 may include a controller 110, a power/RF inverter stage 120, and a feedback circuit 130. The power/RF inverter stage 120 may receive power from a power source 104. The controller 110 may control the power/RF inverter stage 120 to provide an output signal that may be used to perform a procedure on a patient. The feedback circuit 130 may provide feedback information (e.g., voltage, current, temperature, etc.) to the controller 110. The controller 110 may adjust the power/RF inverter stage 120 to modify the output signal based on the feedback information.

Figure 2:
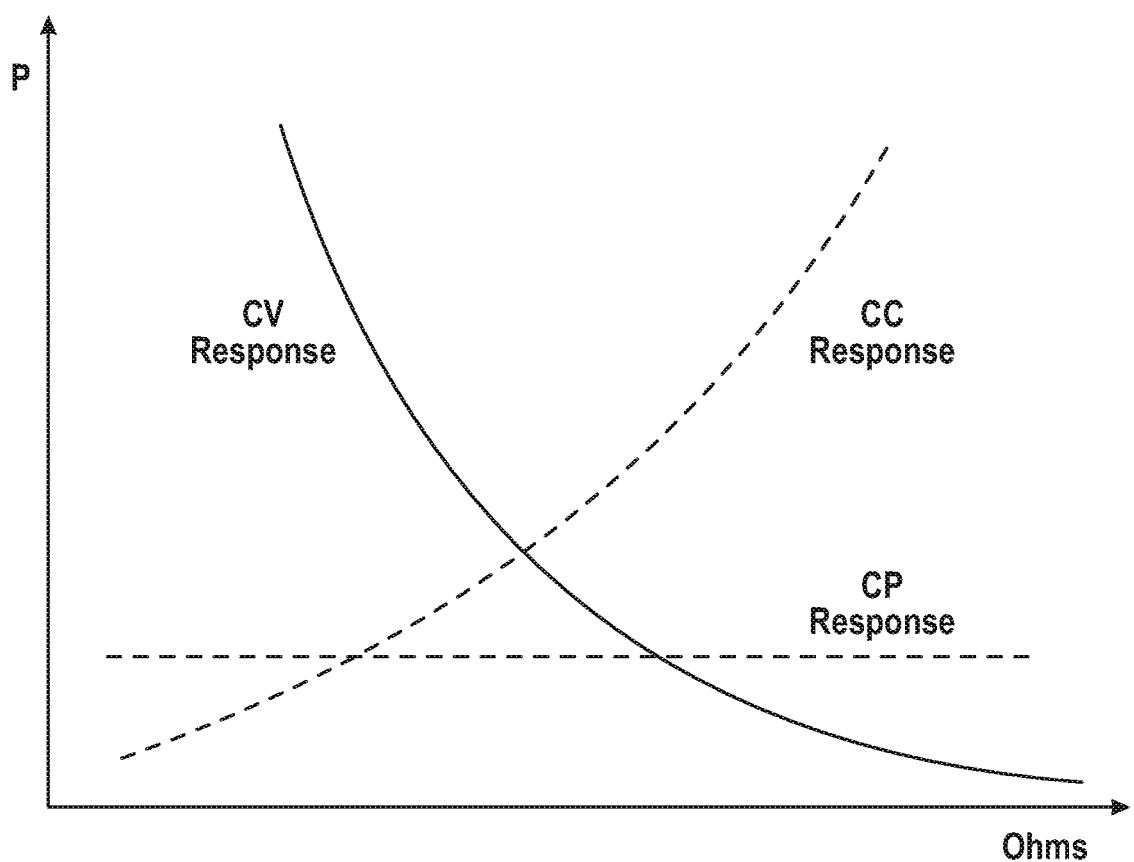
FIG. 2 is an example constant power, voltage, and current impedance load curve according to embodiments of the disclosure.

In general, control of the medical device 100 may be achieved through some combination of temperature feedback and impedance feedback (load curves). Load curves used in the medical device 100 define how much power to deliver to tissue at a particular impedance. These load curves typically have constant current (CC), constant power (CP), and/or constant voltage (CV) regions. FIG. 2 is an example constant power, voltage, and current impedance load curve according to embodiments of the disclosure. In FIG. 2, the "CP" refers to a constant power load curve, the "CC" refers to a constant current, and the "CV" refers to constant voltage. Each of the CP, CC, and CV load curves illustrate how power consumption (P) changes over various impedance loads (Ohms) in the three control scenarios.

In electrosurgery, it may be necessary to regulate output power from the power/RF inverter stage 120 with load change and/or temperature change. One method of output power regulation may include changing input direct current (DC) voltage to the inverter stage of the power/RF inverter stage 120 by a buck or boost converter. Although simple, this cascaded configuration may increase power loss, size, and cost of the medical device 100. Rather than providing a static DC supply to a variable buck stage at the power source 104, and providing the output of the buck stage to the power/RF inverter stage 120, a static DC rail may be directly connected to the power/RF inverter stage 120 from the power source. The DC rail may come from rectified mains, alternating current (AC)/DC supply, or a battery.

Therefore, in some examples, the medical device 100 may include a direct control implementation where the power/RF inverter stage 120 receives direct current (DC) rail power derived from an off-the-shelf alternating current (AC)/DC power supply, rectified mains power (e.g., 240 V), or a battery via the power source 104, and the controller 110 controls the power/RF inverter stage 120 to perform power scaling and conversion from DC power to AC power. This may simplify the design to a single stage, reducing cost, size, and power loss due to additional circuitry and multiple conversions. The power levels, duty cycle, and frequency of the output signal provided from the power/RF inverter stage 120 to the patient may be based on the selected therapy.

In some examples, the controller 110 may implement a mixed signal controller that includes an analog control loop (e.g., inner loop) circuit and a digital control loop (e.g., outer loop) circuit to control the power/RF inverter stage 120 and/or the power source 104. The digital control loop may provide set points for voltage, current, power, and/or temperature to the analog control loop, and the analog control loop may control the power/RF inverter stage 120 based on a comparison between direct feedback voltage, current, power, and/or temperature from the output of the power/RF inverter stage 120 with the voltage, current, power and/or temperature setpoints received via the digital control loop.

In order to achieve a tradeoff between fast response times and intelligence of control, a mixed signal controller combines flexibility of a digital/programmable controller to define different therapies (current, power, voltage, temperature setpoints) with accuracy and responsiveness of an analog controller to execute and maintain requested setpoints and to transition among constant current, constant voltage, and constant power control. A mixed signal controller is setup as a single or multi-loop controller, where the analog controller forms an inner loop, and the digital controller forms an outer loop or can act as a supervisor.

Generally, the power/RF inverter stage 120 may provide an output signal that has a sinusoidal waveform to the patient. The switches 122 of the power/RF inverter stage 120 may be controlled to convert the DC signal to a signal that has a periodic waveform. The waveform out of the switches 122 may be a square waveform, in some examples. The transformer and filter stage 124 may receive the square waveform signal from the switches 122, and may filter and/or amplify the square wave signal to provide a sinusoidal waveform signal as an output to the patient. In some examples, the transformer and filter stage 124 may include a resonant isolated transformer to achieve desired signal characteristics, such as frequency, amplitude, etc. by providing both load independent gain and filtering. Implementing a resonant isolated transformer may reduce size and cost, as compared with a multi component transformer and inductor implementation. The transformer and filter stage 124 may include at least one of the following types of circuitry: voltage in/voltage out, voltage in/current out, current in/current out, and current in/voltage out.

In some examples, the feedback circuitry may also include safety circuitry that monitors output power, voltage, current and/or temperature. The safety circuitry may cause the medical device 100 to shut down in response to detecting an unsafe condition.

Direct Control Topology

Figure 3A:
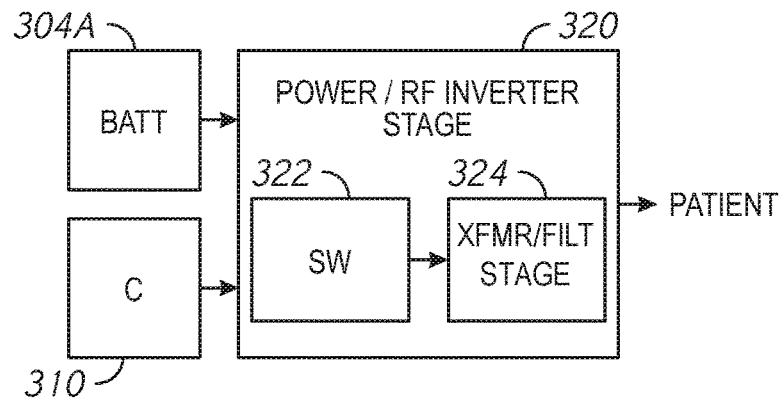
FIGS. 3A-3C are block diagrams of example medical devices including direct drive topology controllers according to embodiments of the disclosure.
Figure 3B:
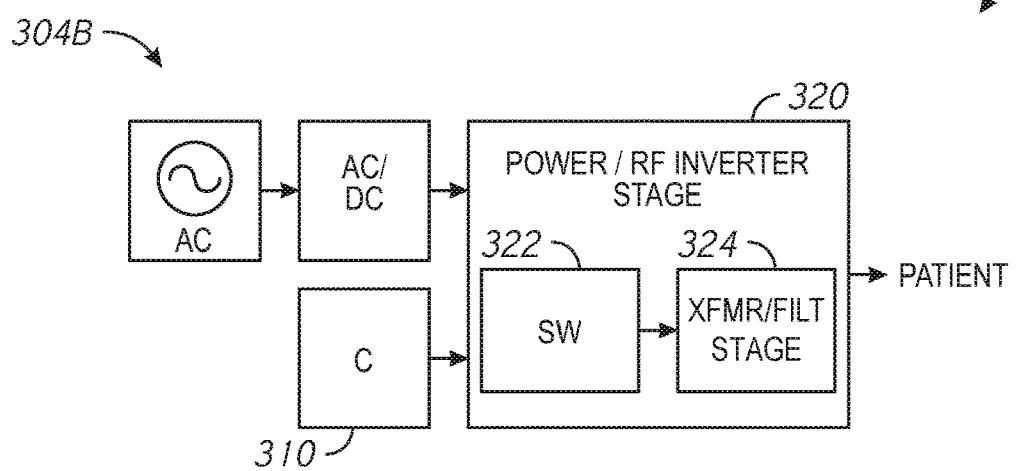
Figure 3C:
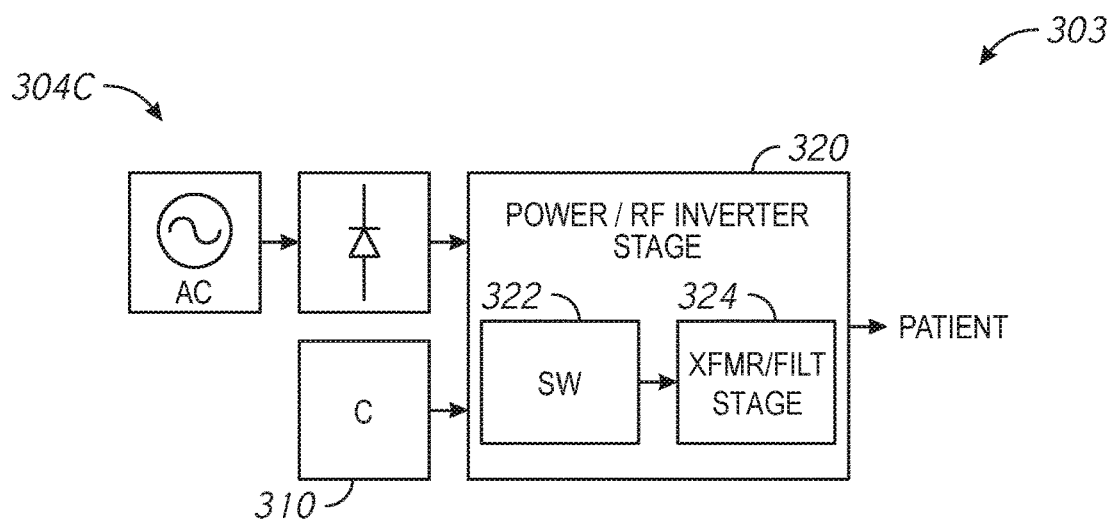
Figure 4:
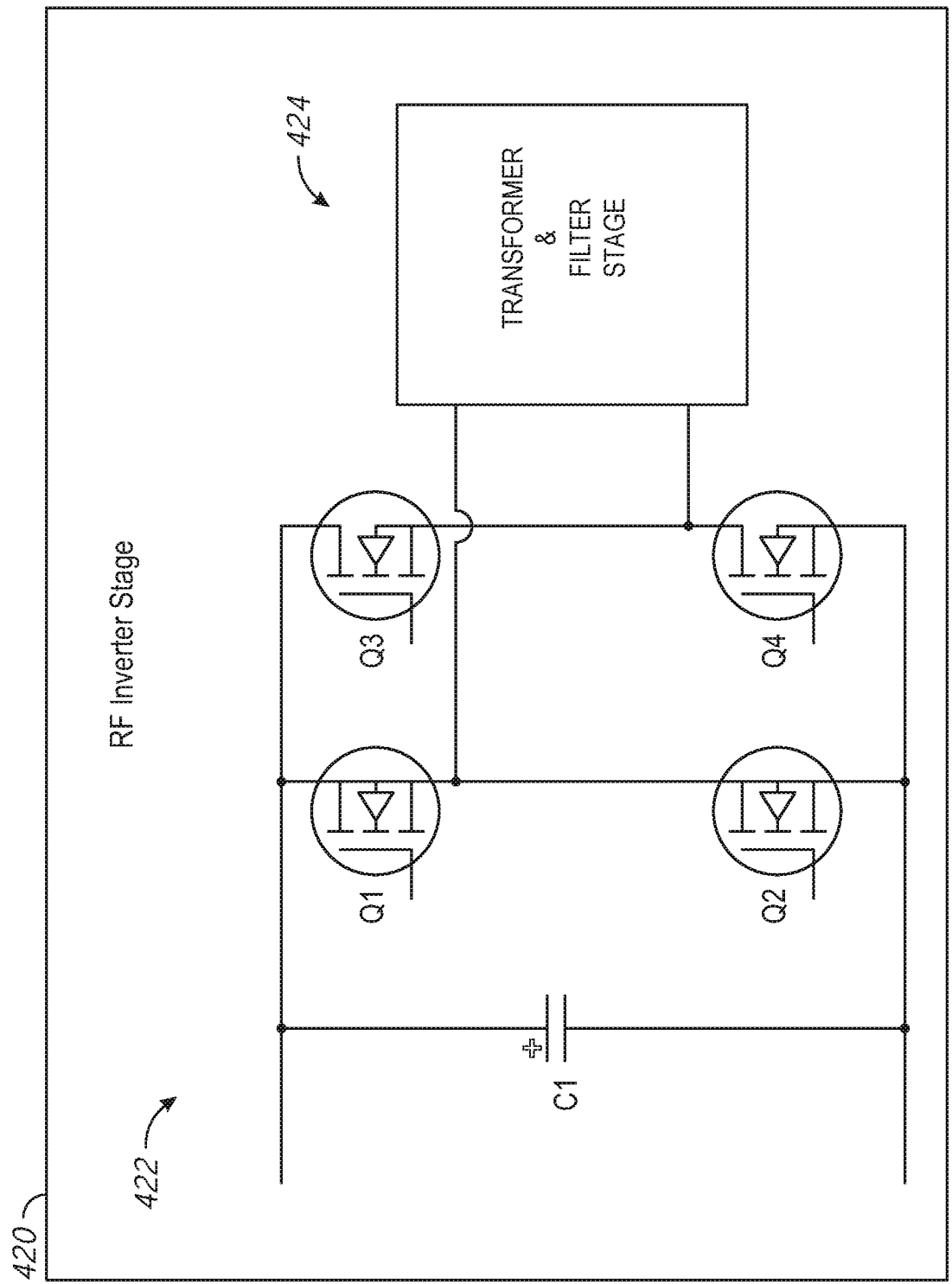
FIG. 4 is a block diagram of an example medical device including an RF inverter stage according to embodiments of the disclosure.

FIGS. 3-4 depict examples of a direct drive implementation of a medical device implementing a direct control topology according to embodiments of the disclosure. FIGS. 3A-3C depict example medical devices 301, 302, and 303, respectively. The medical devices 301, 302, and 303 have common reference numbers for common components, and description of those common reference numbers will not be repeated in the interest of brevity. The medical devices 301, 302, and 303 may be implemented in the medical device 100 of FIG. 1.

The medical devices 301, 302, and 303 may each include a controller 310, a power/RF inverter stage 320, and a power supply 304 (A-C). The power/RF inverter stage 320 includes switches 322 coupled to a transformer and filter stage 324. The controller 310 may be implemented in the controller 110 of FIG. 1 and/or the power/RF inverter stage 320 may be implemented in the power/RF inverter stage 120 of FIG. 1. The differences between the medical devices 301, 302, and 303 are the power supply. The medical device 301 may use a battery 304A as a power source. The medical device 302 may use a DC power source 304B as a power source. The medical device 303 may use a rectified main power source 304C as a power source. The controller 310 may control the power/RF inverter stage 320 to provide an output signal that may be used to perform a procedure on a patient. In some examples the medical devices 301, 302, and 303 may further include a feedback circuit that provides feedback voltage, current, power and/or temperature to the controller 310. The controller 310 may adjust the power/RF inverter stage 320 to modify the output signal based on the feedback signal.

In electrosurgery, it may be necessary to regulate output power from the power/RF inverter stage 320 with load change. In the medical devices 301, 302, and 303, the power/RF inverter stage 320 may be directly connected to a DC rail power source (e.g., the respective battery 304A, AC/DC power source 304B, or rectified main power source 304C)

The controller 310 may include a direct control implementation of the power/RF inverter stage 320 to perform power scaling and conversion from DC to AC waveforms. This may simplify the design to a single stage, reducing cost, size, and power loss due to additional circuitry and multiple conversions. The power levels, duty cycle, and frequency of the output signal provided from the power/RF inverter stage 120 to the patient may be based on the selected therapy.

FIG. 4 depicts an example of an RF inverter stage 420 according to an embodiment of the disclosure. The RF inverter stage 420 may be implemented in the power/RF inverter stage 120 of FIG. 1 or the power/RF inverter stage 320 of FIGS. 3A-3C. The RF inverter stage 420 may include an H-bridge inverter 422 coupled to a RF transformer and filter (e.g., inductors and capacitors) stage 424. The H-bridge inverter 422 may include 4 independent control signal inputs for each of transistors Q1-Q4. The controller (not shown) (e.g., the controller 110 of FIG. 1 and/or the controllers 310 of FIGS. 3A-3C) may manipulate control signals to those inputs to provide an output signal to the transformer and filter 424. In some examples, the controller may cause the H-bridge inverter 422 to convert a DC power signal to an AC signal having a square waveform using those control signals.

Use of single stage conversion as depicted in the power/RF inverter stage 320 of medical devices 301, 302, and 303 of FIGS. 3A-3C, respectively, and the RF inverter stage 420 of FIG. 4 may be advantageous from size, price and potential efficiency savings, but it presents a new set of challenges as compared with an implementation that includes more than one stage. Power conversion at high frequency may suffer from high switching losses unless zero voltage (ZVS) or zero current switching (ZCS) schemes are used. These schemes may be difficult to maintain for all operating conditions. In prior topologies only load changes had to be accommodated to maintain ZVS/ZCS, where changing power was done by a preceding power stage. In the single stage topology, variable load and variable inverter duty cycle may have to be accommodated to maintain ZVS. The following control approach may implement one or more techniques to accomplish low switching losses and maintain high efficiency.

Figure 12:
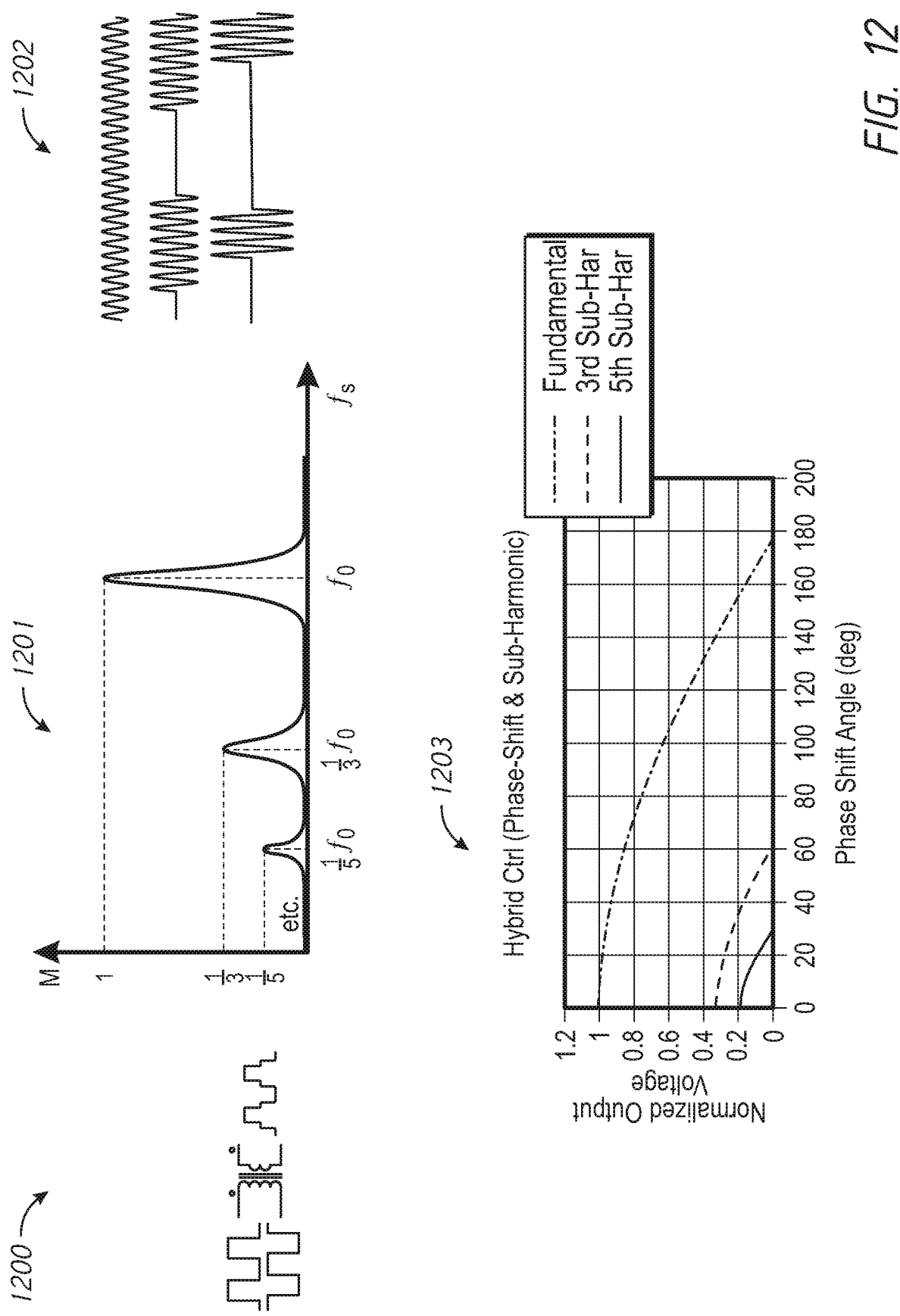
FIG. 12 depicts illustrations for three types of control of output power of the H-bridge inverter in accordance with embodiments of the disclosure.

For example, output power control may be accomplished by direct control of the H-bridge inverter 422 using one or more of following techniques. A first technique (e.g., phase shift mode control) may include varying phase shift angle of the H-bridge inverter 422. This may directly control the fundamental amplitude of the output voltage. A second technique (e.g., subharmonic frequency mode control) may include reducing inverter frequency to sub harmonics of a fundamental frequency. This may reduce the output voltage in integer increments, such as $\frac{1}{3}$, $\frac{1}{5}$, etc. A third technique (e.g., amplitude modulation mode control) may include duty cycle control over many fundamental frequency periods. This may inject power in bursts, such that an average power is proportional to duty cycle. FIG. 12 depicts illustrations for three types of control of output power of the H-bridge inverter in accordance with embodiments of the disclosure. For example, the diagram 1200 depicts an example of amplitude control using phase shift mode control. Diagram 1201 depicts an example of amplitude control using subharmonic frequency mode control. Diagram 1202 depicts an example of amplitude control using duty cycle changes (e.g., amplitude modulation mode control).

A control signal from a controller may be used to control amplitude of high frequency carrier signal (e.g., around 500 kHz) in some examples. The control signal should be able to effectively scale input DC voltage using phase shift control of the H-bridge inverter 422 (e.g., as shown in diagram 1200 of FIG. 12). For low output voltages, use of phase shift control may become inefficient and generates excessive electromagnetic interference (EMI). To help with these two issues, additional signal modulation may be implemented in conjunction with phase shift control or in place of phase shift control.

Because using phase shift mode control alone may not be suitable for all scenarios, other mode control solutions may be combined with the phase shift control mode. For example, a first combined mode control option may include use of subharmonic modes (e.g., as shown in diagram 1201) in combination with the phase shift control mode. In this example, a drive frequency may be changed to subharmonic of carrier. With every subharmonic step down available peak voltage is reduced appropriately and as a result the control signal can be rescaled over a smaller control range. The example diagram 1203 of FIG. 12 shows exemplary peak voltage variation using one combined implementation that includes one type of a phase-shift mode control and one type of a subharmonic frequency mode control.

A second combined mode control option may include amplitude modulation mode control (e.g., modulating the carrier over many cycles (e.g., at 20 kHz) and effectively reducing average input voltage to the inverter 1202) in combination with the phase shift mode control. This may allow a control signal to be rescaled over a smaller control range.

From the above two combined mode control options, the first combined mode control option (e.g., using phase-shift and subharmonic modulation) may be preferred when uninterrupted patient signal is required, like in cut mode. In other modes (e.g., such as coagulation mode), where thermal spread in the tissue is expected, an interrupted carrier waveform may be preferred. In such cases, the second combined mode control option (e.g., duty cycle modulation) may be used.

Figure 5:
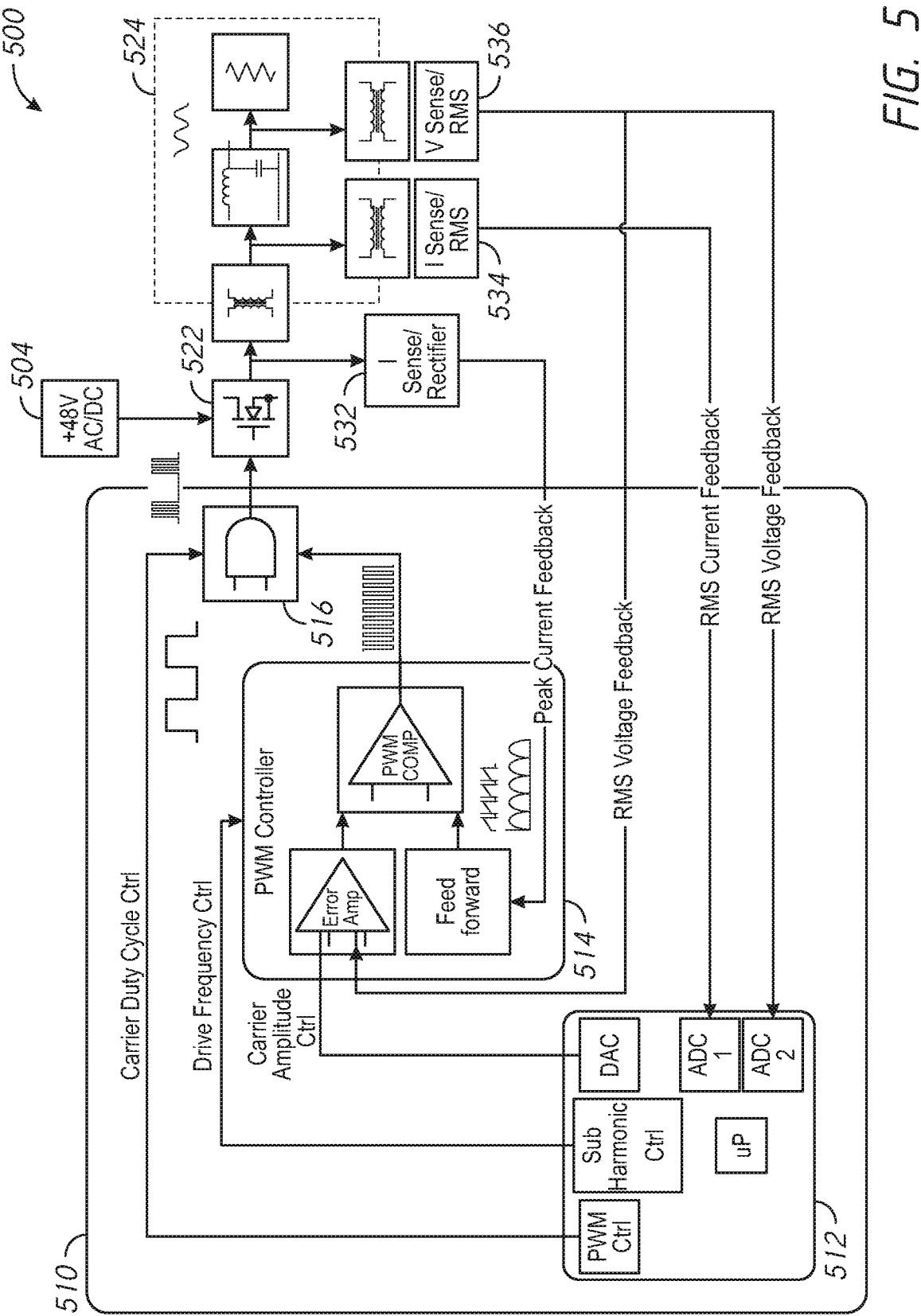
FIG. 5 is a block diagram of an example medical device including a direct drive topology controller according to embodiments of the disclosure.

FIG. 5 depicts a specific example of a medical device 500 using direct drive topology according to an embodiment of the disclosure. The medical device 500 may include a controller 510, and switches 522 and transformer and filter stage 524 that form a power/RF inverter. The controller 510 may be implemented in the controller 110 of FIG. 1 and/or the controller 310 of FIGS. 3A-3C, the switches 522 may be implemented in the switches 122 of FIG. 1, the switches 322 of FIGS. 3A-3C, and/or the H-bridge inverter 422 of FIG. 4, and the transformer and filter stage 524 may be implemented in the transformer and filter stage 124 of FIG. 1, the transformer and filter stage 324 of FIGS. 3A-3C, and/or the transformer and filter stage 424 of FIG. 4.

The controller 510 may implement a control mode that includes one or more of a varying phase shift angle control mode, use of subharmonic frequency control modes, or duty cycle modulation control mode using a digital controller 512 and/or a pulse width modulator (PWM) controller 514. The digital controller 512 may include a PWM control module, a subharmonic control module, a microprocessor, and analog-to-digital (ADC) converters for feedback signals, and digital-to-analog (DAC) converter to provide control signals. The digital controller 512 may also include analog-to-digital converters (ADCs) 1 and 2 that are configured to receive root-mean-square (RMS) current feedback and RMS voltage feedback signals, respectively. The PWM control module of the digital controller 512 may provide a carrier duty cycle control signal based on the RMS current and RMS voltage feedback signals when using a duty cycle control mode. The subharmonic control of the digital controller 512 may provide a drive frequency control signal based on the RMS current and RMS voltage feedback signals when using a subharmonic frequency control mode. The DAC of the digital controller 512 may provide a carrier amplitude control signal based on the RMS current and RMS voltage feedback signals when using a phase shift angle control mode. In some examples, the RMS current and voltage feedback may include complex feedback.

The PWM controller 514 may include an error amplifier that compares the carrier amplitude control signal from the digital controller 512 with the RMS voltage feedback signal, a feedforward compensator that provides a control signal based on the peak current feedback signal from a sense rectifier 532, and a PWM comparator to provide an output signal based on signals from the error amplifier and the feedforward compensator.

The controller 510 may further include a logic gate 516 that compares an output of the PWM comparator of the PWM controller 514 with the carrier duty cycle control signal from the PWM control module of the digital controller 512 to provide an output control signal to switches 522. The logic gate 516 may include an AND logic gate, in some examples. The switches 522 may provide power signals to the transformer and filter stage 524 and to the sense/rectifier 532 based on the output control signal and based on power from a DC power source, such as the +48 V AC/DC power source 504. The transformer and filter stage 524 may filter and amplify the power signal from the switches 522 to provide an output signal to the patient. The transformer and filter stage 524 may include a transformer and an inductor-capacitor (LC) circuit, in some examples. The sense/rectifier 532 provides the peak input current feedback signal to the PWM controller 514. The root-mean-square (RMS) current sensor 534 and the RMS voltage sensor 536 provide RMS current and voltage feedback signals, respectively, to the digital controller 512 based on a sensed output.

Mixed Signal Controller

Figure 6:
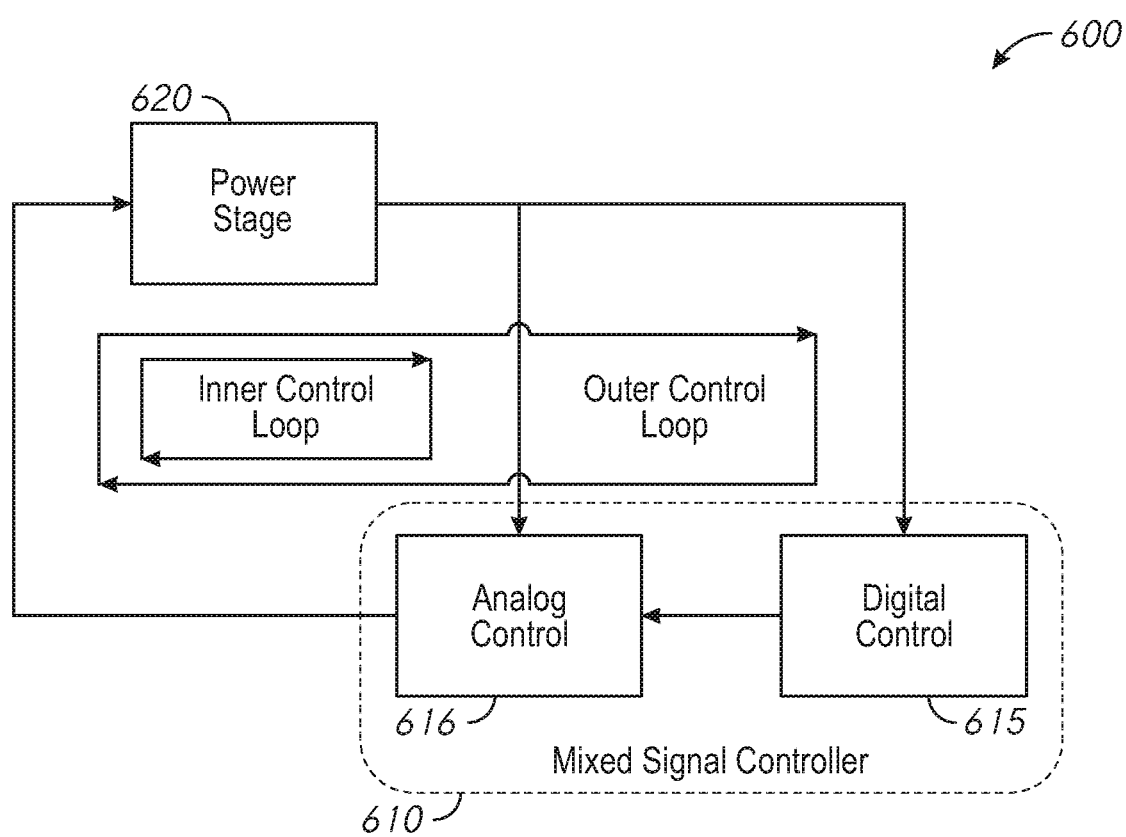
FIG. 6 is a block diagram of an example medical device including a mixed signal controller according to embodiments of the disclosure.
Figure 7:
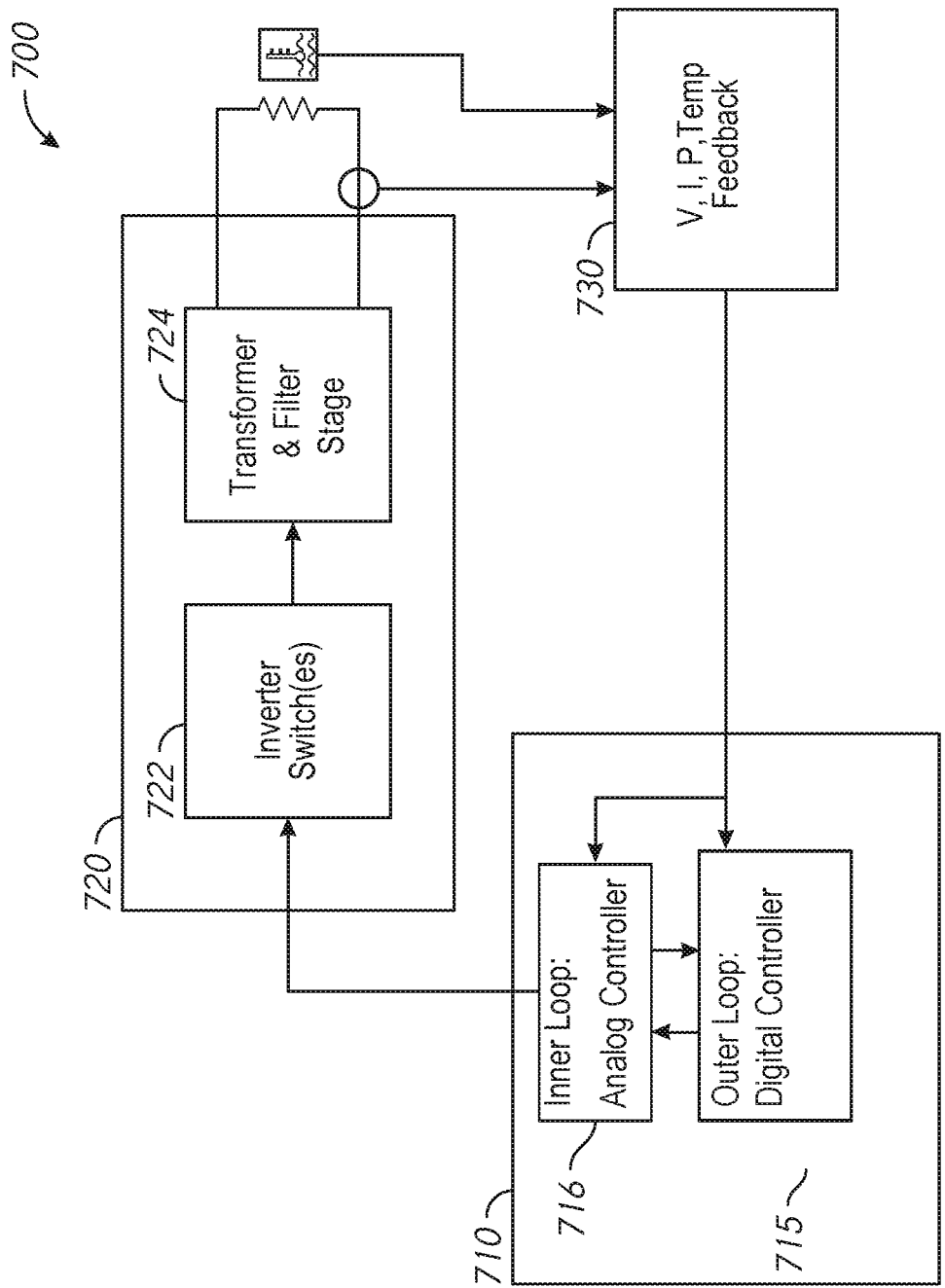
FIG. 7 is a block diagram of an example medical device including a mixed signal controller according to embodiments of the disclosure.
Figure 8:
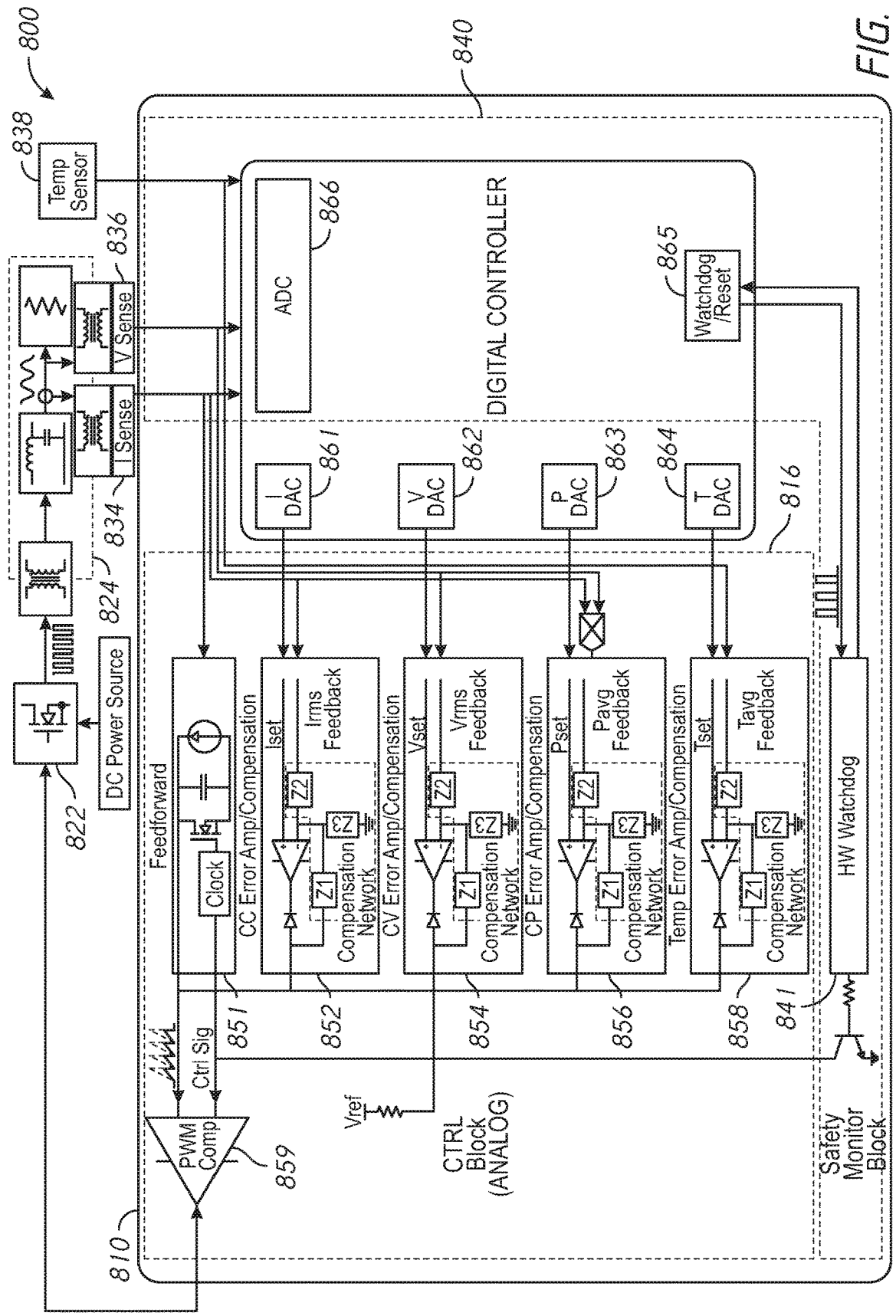
FIG. 8 is a block diagram of an example medical device including a mixed signal controller according to embodiments of the disclosure.

FIGS. 6-8 depict examples of a mixed signal controller implementation of a medical device 600 according to embodiments of the disclosure. FIG. 6 is a block diagram of a medical device 600 with a mixed signal controller 610 in accordance with some embodiments. The medical device 600 may include a mixed signal controller 610 coupled to a power stage 620. The mixed signal controller 610 may be implemented in the controller 110 of FIG. 1, the controller 310 of FIGS. 3A-3C, the controller 510 of FIG. 5, or combinations thereof. The power stage 620 may be implemented in the power/RF inverter stage 120 of FIG. 1, the power/RF inverter stage 320 of FIGS. 3A-3C, the RF inverter stage 420 of FIG. 4, the switches 522 and/or transformer and filter stage 524 of FIG. 5, or combinations thereof.

The mixed signal controller 610 may include a digital controller 615 and an analog controller 616. The analog controller 616 and the power stage 620 may form an inner loop to control CV, CC, CP, temperature, or other parameters that may be used by the analog controller 616. The digital controller 615, the analog controller 616, and the power stage 620 may form an outer loop to control setpoints of CV, CC, CP, temperature, or other parameters that may be used by the analog controller 616 to control the output signal of the power stage 620.

As shown in FIG. 6, this mixed signal topology utilizes two control loops. The inner control loop may be an analog control loop whereby the analog controller 616 uses analog circuitry to adjust the output signals to the power stage 620 based on output signals from the power stage 620, and the outer loop may be a digital control loop whereby the digital controller 615 uses digital circuitry to adjust the input signals provided to the analog controller 616 based on output signals from the power stage 620, and in some examples, additional inputs or feedback from other patient measurements, such as temperature. That is, in the outer digital loop, the digital controller 615 may be responsible for setting CC, CP, CV, and/or temperature setpoints/levels, that specify load curve outlines and different therapies. In the inner loop, the analog controller 616 may be tasked with complying with these limits. The digital controller 615 may change input setpoints to the inner loop in response to other control parameters that may be monitored by digital controller 615, such as temperature, pressure, time, and/or user inputs. The digital controller 615 may monitor the voltage and current feedback to calculate the impedance, which may be used to determine whether to set or adjust a CC, CP, or CV setpoint based on the desired power profile.

FIG. 7 is a block diagram of a medical device 700 with a mixed signal controller 710 in accordance with some embodiments. The medical device 700 may include a controller 710 coupled to an RF inverter stage 720 and to a feedback circuit 730. The controller 710 may be implemented in the controller 110 of FIG. 1, the controller 310 of FIGS. 3A-3C, the controller 510 of FIG. 5, the mixed signal controller 610 of FIG. 6, or combinations thereof. The RF inverter stage 720 may be implemented in the power/RF inverter stage 120 of FIG. 1, the power/RF inverter stage 320 of FIGS. 3A-3C, the RF inverter stage 420 of FIG. 4, the switches 522 and/or transformer and filter stage 524 of FIG. 5, the power stage 620 of FIG. 6, or combinations thereof.

The controller 710 may include a digital controller 715 and an analog controller 716. The analog controller 716, the RF inverter stage 720, and the feedback circuit 730 may form an inner loop to control the RF inverter stage 720 to provide the output signal having desired characteristics for the selected therapy. The digital controller 715, the analog controller 716, the RF inverter stage 720, and the feedback circuit 730 may form an outer loop to control or set CV, CC, CP, temperature setpoints/levels, or other parameters that may be used by the analog controller 716 to control the output signal of the RF inverter stage 720. The control signals provided by the analog controller 716 may control circuitry of the inverter switches 722 and filtering of the transformer and filter stage 724 to provide the output signal. The feedback circuit 730 may provide feedback signals related to voltage, current, and temperature (e.g., from a temperature sensor) back to the digital controller 715 and the analog controller 716. The digital controller 715 may adjust the setpoints based on the mode of operation and based on the feedback signals from the 730. The analog controller 716 may adjust the output signal based on a comparison between the setpoints and the feedback signals from the feedback circuit 730.

FIG. 8 is a detailed diagram of an example medical device 800 with a mixed signal controller 810 in accordance with some embodiments. The medical device 800 may include a controller 810 coupled to a power stage (e.g., including inverter switches 822 and transformer and filter stage 824) and to a feedback circuit (e.g., including a current feedback circuit 834, a voltage feedback circuit 836, and a temperature feedback circuit 838). The medical device 800 may further include a safety monitor block 840. The controller 810 may be implemented in the controller 110 of FIG. 1, the controller 310 of FIGS. 3A-3C, the controller 510 of FIG. 5, the mixed signal controller 610 of FIG. 6, the controller 710 of FIG. 7, or combinations thereof. The 820 may be implemented in the power/RF inverter stage 120 of FIG. 1, the power/RF inverter stage 320 of FIGS. 3A-3C, the RF inverter stage 420 of FIG. 4, the switches 522 and/or transformer and filter stage 524 of FIG. 5, the power stage 620 of FIG. 6, the power stage 620 of FIG. 7, or combinations thereof. The current feedback circuit 834, the voltage feedback circuit 836, and the temperature feedback circuit 838 may be implemented in the feedback circuit 130 of FIG. 1, the feedback circuit 730 of FIG. 7, or combinations thereof.

The controller 810 may include a digital controller 815 and a control block (analog) 816. The control block (analog) (hereafter analog controller) 816 may include a feedforward compensator 851, a CC error compensator 852, a CV error compensator 854, a CP error compensator 856, and a temperature error compensator 858. The feedforward compensator 851 provides corrections for load-current perturbations. The corrections applied by the feedforward compensator 851 may be applied to control signal in the form of a variable PWM ramp. The PWM ramp amplitude may include a simple linear function of output current. The PWM ramp may be made proportional to an output current by integrating voltage proportional to the output current with a resettable integrator that is reset with a clock pulse. The CC error compensator 852, the CV error compensator 854, the CP error compensator 856, and the temperature error compensator 858 may receive respective sensed voltage, current, and/or temperature signals, and may adjust corresponding output signals based on a comparison with a corresponding setpoint signal (e.g., Iset, Vset, Pset, and Tset, respectively). The setpoint signals are provided from the digital controller 815.

The digital controller 815 includes a current (I) DAC 861, a voltage (V) DAC 862, a power (P) DAC 863, and a temperature (T) DAC 864 that provide the Iset, Vset, Pset, and Tset signals, respectively, to the analog controller 816. The digital controller 815 further includes an ADC 866 that converts the sensed voltage, current, and temperature signals to digital signals. The current DAC 861, the voltage DAC 862, the power DAC 863, and the temperature DAC 864 may set the Iset, Vset, Pset, and Tset signals, respectively, based on the converted voltage, current, and temperature signals.

The analog controller 816, the inverter switches 822, the transformer and filter stage 824 and the feedback circuit (e.g., the current feedback circuit 834 and the voltage feedback circuit 836) may form an inner loop to control the inverter switches 822 and the transformer and filter stage 824 to provide the output signal having desired characteristics for the selected therapy. The digital controller 815, the analog controller 816, the inverter switches 822, the transformer and filter stage 824 and to the feedback circuit (e.g., the current feedback circuit 834 and the voltage feedback circuit 836) may form an outer loop to control CV, CC, CP, temperature setpoints (e.g., Iset, Vset, Pset, and Tset signals), or other parameters that may be used by the analog controller 816 to control the output signal of the inverter switches 822 and the transformer and filter stage 824.

The following discussion regarding the mixed-signal controller may refer to components of any of the mixed signal controller 610, the controller 710, or the controller 810. While the following discussion describes operation of a controller in the context of ESUs, the controller 610, the controller 710, or the controller 810 are not limited to such applications. Electrosurgery is a process of delivering high frequency electrical current to biological tissue to achieve medically relevant thermal effect. Tissue thermal effects depend on final temperature of the tissue and how fast the tissue was heated. Tissue temperature and temperature change rate can be monitored and controlled directly or inferred from tissue impedance. Tissue impedance is derived from measured output voltage and current. Thermal effects may include tissue ablation, tissue cutting, and/or tissue removal, and may occur at the surface of the tissue or under the surface of the tissue.

In some examples, control of ESUs (and other medical devices) may be achieved through some combination of temperature feedback and impedance feedback (load curves). Load curves (e.g., refer to FIG. 2) used in ESU define how much power to deliver to tissue at a specific impedance. These load curves typically have CC, CP, and CV regions.

Disclosed mixed signal controller combines flexibility of a digital/programmable controller to define different therapies (e.g., current, power, voltage, temperature set points) with accuracy and responsiveness of an analog controller to execute and maintain requested set points. The mixed signal controller may be setup as single or multi-loop controller, where the analog controller forms an inner loop, and the digital controller forms an outer loop (or can act as a supervisory circuit/controller or can act to accept or change different load curve configurations).

The analog controller may include load shaping CC, CP, CV error amplifiers (e.g., see error amplifiers of the CC error compensator 852, the CV error compensator 854, and the CP error compensator 856 of the analog controller 816 of FIG. 8) and constant temperature error amplifier (thermostatic controller) (e.g., see the error amplifier of the temperature error compensator 858 of the analog controller 816 of FIG. 8). A requested load curve may be conditional to the thermostatic controller. A sensed output voltage, current, and temperature may be used as feedback for the error amplifiers, where setpoints come from the digital/programmable controller (e.g., see the current (I) 861, voltage (V) 862, power (P) 863, and temperature (T) 864 DACs of the digital controller 815 of FIG. 8).

Each error amplifier may form a closed control loop for an associated control parameter. These loops may run in parallel. A response time (loop gain) of each closed loop may be setup by associated compensation network. The error amplifiers may be combined with minimum output selector to derive control signal.

Depending on power levels and electrode type, biological tissue impedance can be very dynamic during the procedure. To improve load transient response and to stabilize the loop gain of error amplifiers, feedback control is combined with load-current feedforward control (e.g., see the feedforward control 851 of the analog controller 816 of FIG. 8). The load-current feedforward control may provide corrections for load-current perturbations. The corrections may be applied to control signal in the form of variable pulse width modulation (PWM) ramp. The PWM ramp amplitude may include a simple linear function of output current. The PWM ramp may be made proportional to an output current by integrating voltage proportional to the output current with a resettable integrator that is reset with a clock pulse.

The derived control signal from the error amplifiers and the PWM ramp from load-current feedforward control may be combined with PWM comparator 859 to drive the switch mode inverter amplifiers (e.g., see the inverter switches 822 of FIG. 8).

In specific reference to operation of the circuitry of the analog controller 816 and the digital controller 815, load current, voltage, and power may be read directly from the output of the transformer and filter stage 824. All measurements may be performed with isolated sense transformers to maintain patient electrical safety isolation barrier. The analog controller 816 may include several feedback loops, e.g., a constant current loop (e.g., including the CC error compensator 852), a constant voltage loop (e.g., including the CV error compensator 854), a constant power loop (e.g., including the CP error compensator 856), and a constant temperature loop (e.g., including the temperature error compensator 858), which transition automatically from CC to CP to CV to CT control and vice versa after output reaches outer loop defined target setting. The digital controller 815 may include DACs (e.g., current (I) 861, voltage (V) 862, power (P) 863, and temperature (T) 864 DACs) to set the target current, voltage, power, and temperature for CC, CV, CP, and CT analog feedback loops respectively. The analog feedback loops may be implemented with precision error amplifiers and compensation networks (e.g., see the error amplifiers and compensation networks of the analog controller 816 of FIG. 8) that set frequency response of analog feedback loop. An analog "NOR" circuit (minimum output selection) combines outputs of error amplifiers and implements the CC-CP-CV-CT algorithm. Output of the analog controller (e.g., a proportional integral derivative (PID) controller) may be used as input to PWM modulator for direct control of power stage.

More specifically (referring to the analog controller 816 of FIG. 8), use of an analog 'NOR' circuit (minimum output selector) to combine CC, CP, CV, and CT error compensators 852, 854, 856, and 858, respectively, to shape specific load curve. Comparing voltage error signal, current error signal, power error signal, and a temperature error signal to decide which error signal may have greater value and limit a patient output signal by the switch mode regulator based on error signal with largest value. A first diode may be coupled to the current amplifier of the CC error compensator 852, a second diode may be coupled to the voltage amplifier of the CV error compensator 854, a third diode may be coupled to the power amplifier of the CP error compensator 856, and a fourth diode may be coupled to the temperature amplifier of the temperature error compensator 858. An anode of first diode, second diode, third diode, and the fourth diode may be tied together and pulled high to determine the largest error signal, which may be used to generate driving signal for switch mode regulator by feeding it into pulse width modulation comparator. It will be appreciated that the analog controller 816 of FIG. 8 may include more or fewer error amplifiers based on desired control parameters, such as adding a pressure signal or elimination of the temperature parameter.

As for the safety monitor block 840, electrosurgical devices may perform their function through application of potentially hazardous high-voltage signals. Yet they must also perform safely and predictably. Because these devices present some risk of harm, they may include safety systems that are fully independent of operational elements of the system. A flawed DAC setpoint value (e.g., Iset from the current (I) DAC 861, Vset from the voltage (V) DAC 862, Pset from the power (P) DAC 863, and/or Tset from the temperature (T) DAC 864) from the digital controller 815 submitted to the analog controller 816 may be mitigated by independent read back (the ADC 866) with "within bounds" check. Because programmable/digital controller 815 is not part of closed control loop, its read back (ADC 866) and setpoint (DAC) blocks may be made independent and as result one can check on the other. As another example, runaway or non-responsive software maybe mitigated by a watchdog check. The safety monitor block 840 may include a hardware watchdog circuit 841 that is periodically serviced by the digital controller 816 via the watchdog/reset module 865 to avoid a system reset.

Some benefits of the mixed signal controller may include:

The analog closed loop, even when it relies on average feedback, may have potential to be faster than an implementation on an average micro controller, which may improve efficacy. Because the digital controller 816 is primarily limited to setting mode crossover points (e.g., CC to CP, CP to CV, etc.), which may be static per therapy, it is unburdened by the RF control and may be scaled down in size/price or may take on other control tasks that are usually reserved for additional microcontrollers, like outer temperature loops or motor control or control of user interface or additional safety monitoring. Another benefit of implementing the RF closed loop in analog is that it is not specific to any one particular microcontroller, and may be replicated in other designs without having to rewrite PID loops every time a different microcontroller is used or application is created. Use of analog control also provides improved accuracy of delivered energy (e.g., analog control offers "infinite" resolution, while dedicated CC, CP, and CV error compensators 852, 854, 856, and 858 keep consistent constant profile), a fast transient load response to feedback signal (e.g., impedance change) may improve efficacy by ensuring proper load curve (e.g., therapies may be defined by specific power or voltage or current or temperature level, and when the levels change, the therapy may change, such as cutting may turn to coagulation or vice versa, and/or the size of the tissue may be less accurate), fast transient response to control signal may allow use of the outer (digital) loop to further shape therapy signal beyond static CC, CV, CP, CT curves (e.g., responsiveness of inner analog loop enables new creative waveforms/therapies), reduction in size/price/development of digital microcontroller or FPGA, and safety critical control is may now be included as part of hardware and does not require as much redundancy mitigation or verification testing.

Resonant Isolated Transformer

As previously discussed electrosurgical generators may deliver an alternating current (AC) signal to patients to achieve a coagulation or cutting effect or for tissue removal. The therapy AC signal may be achieved by inverting a DC signal to provide the AC signal. Part of an RF inverter (power) stage (e.g., the power/RF inverter stage 120 of FIG. 1, the power/RF inverter stage 320 of FIGS. 3A-3C, the RF inverter stage 420 of FIG. 4, the switches 522 and transformer and filter stage 524 of FIG. 5, the power stage 620 of FIG. 6, the RF inverter stage 720 of FIG. 7, and/or the inverter switches 822 and transformer and filter stage 824 of FIG. 8) may include magnetic gain and filtering. Size and price of magnetic components may scale with power, and usually occupies noticeable space in the generator. Reducing either size or price of these components may be beneficial.

Figure 9:
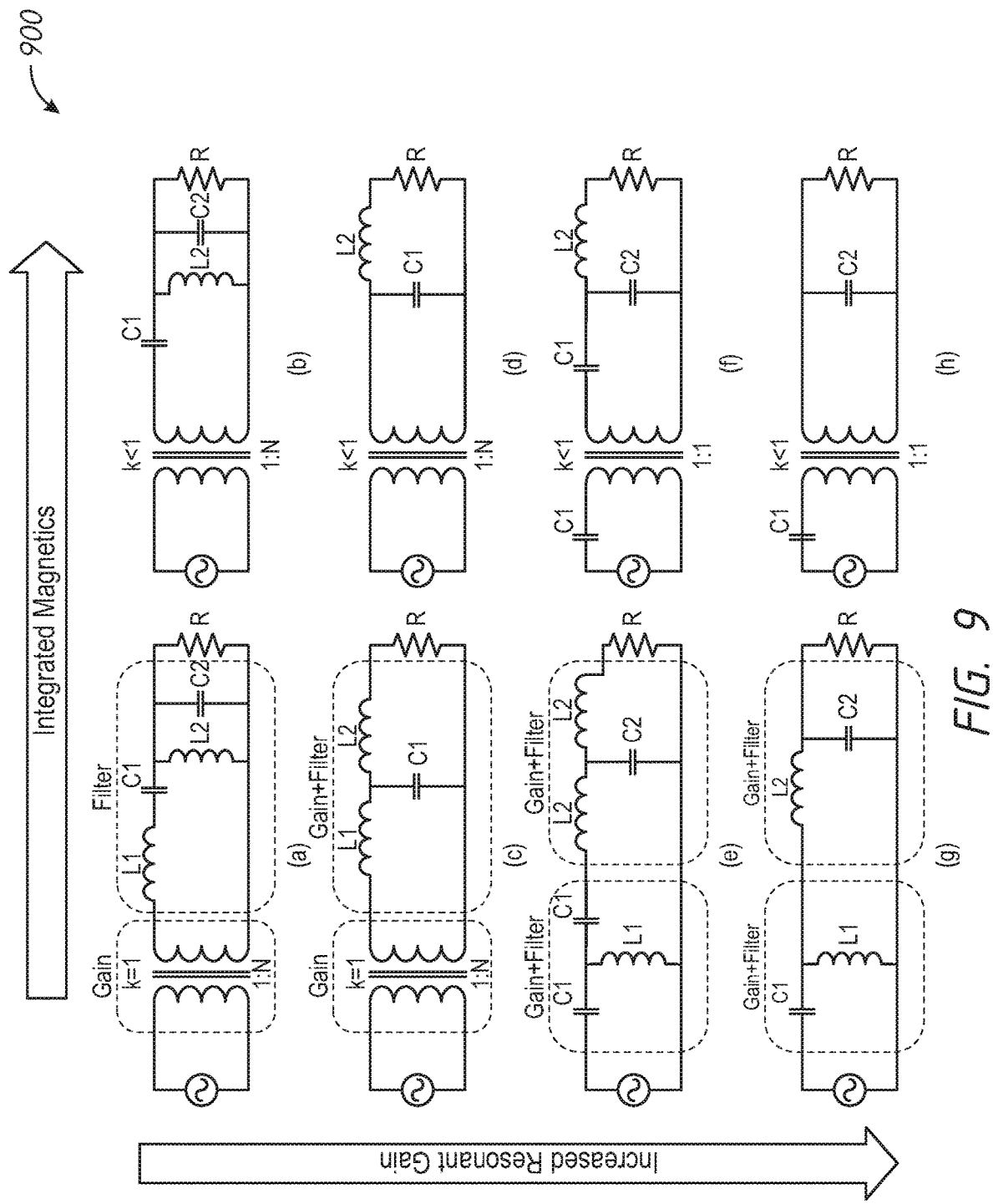
FIG. 9 is a design matrix of RF resonant network circuits according to embodiments of the disclosure.

FIG. 9 is a design matrix 900 of RF resonant network circuits (a)-(h) according to embodiments of the disclosure. A typical approach for the RF inverter stage may include a transformer and filter as shown in the design matrix 900 of circuits (a)-(h) of FIG. 9. The transformer may be responsible for amplification and the filter may remove DC signals and harmonics. Although straight forward, this kind of functional partitioning does not allow full utilization of the magnetic components. With the use of resonant gain, and integrated magnetics it may be possible to optimize use of the transformer and filter (e.g., the transformer and filter stages 124, 324, 424, 524, 724, and/or 824 of FIGS. 1, 3-5, 7, and 8, respectively), and reduce the footprint of the RF inverter stage. In FIG. 9, a design matrix 900 is depicted where progression from top to bottom shows increased use of resonant gain, and progression left to right shows increased use of integrated magnetics.

In circuit (a), a series/parallel LC filter is made up of two impedance compensation networks (series LC, and parallel LC). These networks may store energy proportional to Q and accomplish only filtering. Better use may be made of these reactive elements by using them for impedance transformation, which may accomplish filtering and some gain. For example, when the inductor and capacitor are arranged in an L-network, the circuit may achieve impedance transformation (resonant gain) and filtering. Particular combinations of these L-networks may achieve transformer like voltage gain, which is relatively insensitive to the load (see, e.g., circuit (g)).

Using this concept, it may be possible to completely eliminate the transformer and strictly use a resonant network to achieve all the gain and filtering, which is called a resonance transformer. Topologies in circuits (e) and (g) accomplish just that. However, the resonant network does not provide galvanic isolation, which may be needed for patient protection.

Figure 10:
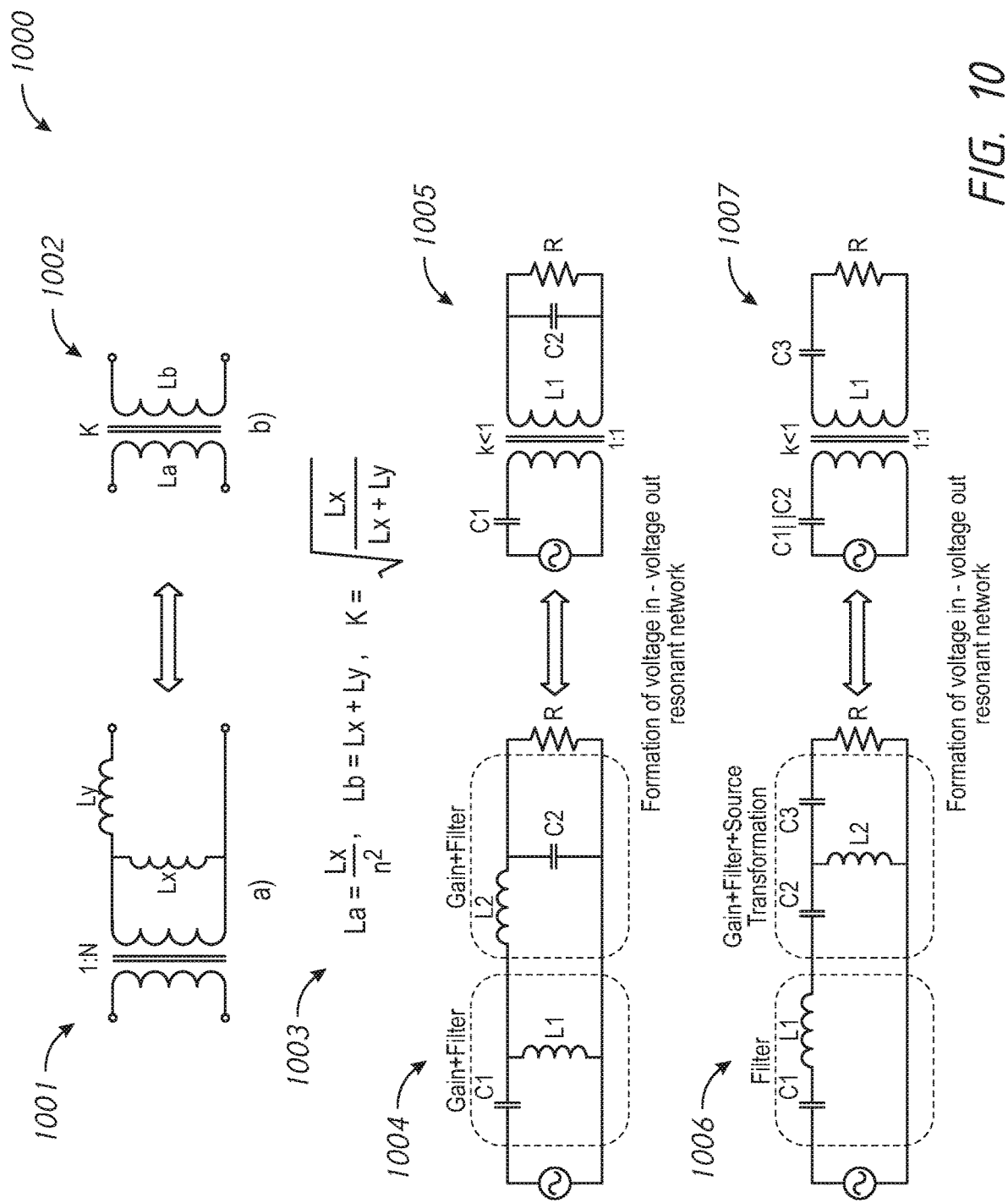
FIG. 10 depicts example RF resonant network circuits according to embodiments of the disclosure.

Integrated magnetics includes absorbing the inductors into a transformer model. Depending on the filter topology, up to two inductors may be integrated into a transformer. FIG. 10 depicts example RF resonant network circuits 1000 according to embodiments of the disclosure. The equivalent transformer model circuit 1001 of FIG. 10 shows three parameters: turns ratio n, magnetizing inductance Lx, and leakage inductance Ly. All of these design parameters may be integrated into a physical transformer shown in the circuit 1002 using the equation 1003. Circuits 1004 and 1005 and circuits 1006 and 1007 depict two examples of using this methodology to derive proposed resonant isolated transformer circuits from a resonant network.

Figure 11:
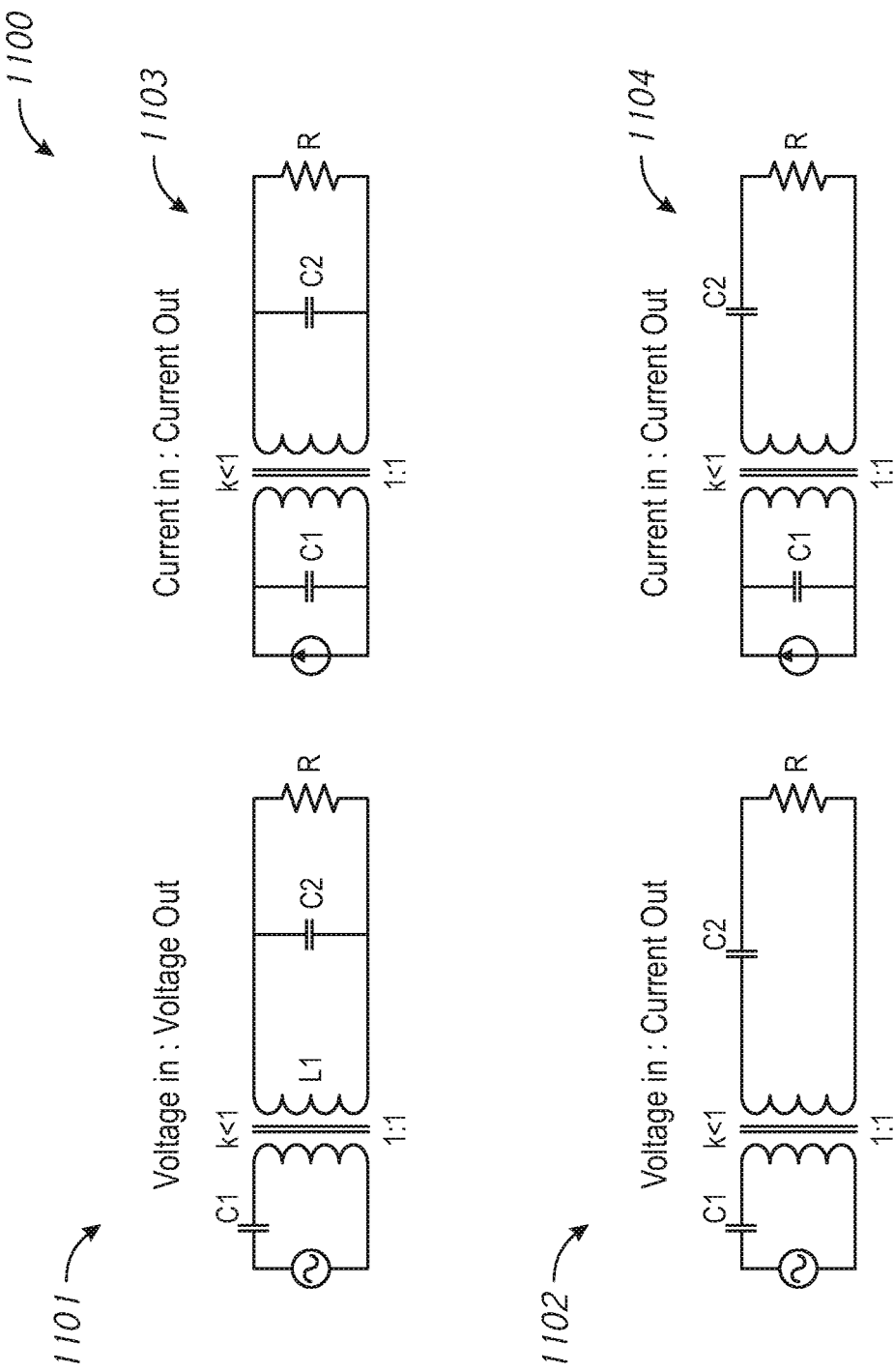
FIG. 11 depicts example RF resonant network circuits according to embodiments of the disclosure.

The RF switch configuration may come in two types: current source, and voltage source. On the other hand, ESU generators (and other medical devices) may come in two types of equivalent output sources: current source, and voltage source. To accommodate either type of RF switch source and ESU output type, one may consider at least one of four types of resonant isolated transformer topologies: voltage in/voltage out (e.g., resistance transformation), voltage in/current out (e.g., transconductance transformation), current in/voltage out (e.g., transresistance transformation), and current in/current out (e.g., conductance transformation). For each topology, a suitable resonant isolated transformer circuit may be designed that provides: load independent gain, a multi-stage filter that minimizes stored energy (optimizes size), uses only one magnetic component (e.g., loosely coupled transformer) in a specified pattern (to accommodate introduction of transformer), and provides appropriate conversion from one source type to another. A resonant isolated transformer has these advantages plus it maintains ZVS condition for all loads, and maintains all associated design properties for a single design frequency. FIG. 11 depicts example RF resonant network circuits according to embodiments of the disclosure. Specifically, FIG. 11 depicts example circuits that for each of these four different topologies. Circuit 1101 is an example of a voltage in/voltage out resonant network, circuit 1102 is an example of a voltage in/current out resonant network, circuit 1103 is an example of a current in/current out resonant network, and circuit 1104 is an example of a current in/current out resonant network.

In some examples, a medical device may include circuitry for only one of these topologies. In other examples, a medical device may include more than one of these topologies that are dynamically selectable based on the intended application. In some examples, rather than wholly separate circuits, some components may be switched in or out in order to switch between the different topologies. In some examples, the switching may be dynamic or may be a one-time switch (e.g., a fuse) to select a desired topology.

The following discussion is a non-limiting discussion of embodiments of the disclosure as it pertains some examples of ESUs in accordance with embodiments of the disclosure:

Electrosurgical units (ESUs) which apply radio frequency (RF) power to electrodes have been used for decades in the general operating room for coagulation and cutting of tissue. Current designs may not be suitable for portable applications due to the following technical limitations. They utilize AC power as the input for the power transfer topology. The power design topology is large due using a two power stage approach: DC converter plus inverter. Finally the use of magnetic components is not optimized resulting in a large output stage. This disclosure presents a topology that is smaller and/or less expensive, which may allow for a portable electrosurgical system or other optimized electrosurgical system to achieve a small, portable ESU generator by replacing AC/DC and variable DC power conversion stages with a small battery, in some examples. To compensate for the lack of a variable DC voltage, direct control of the resonant network may be used to control the output power. Further the use of a resonant and soft-switching drive may reduce a need for heat sinks. Optimizing use of magnetic materials via resonant gain and integrated magnetics may result in smaller footprint of the output magnetics stage. An updated topology for direct drive is shown in FIGS. 3A-3C. For a portable ESU generator, the use of a battery is necessary. With the battery and direct control of the resonant network, the variable DC input stage is eliminated. This reduces efficiency losses due to the extra power stage and increases response time. There are a variety of inverter control methods that are commonly used in switch-mode RF amplifiers.

Direct control of the RF power transfer may be performed using pulse width modulation (PWM) control of the resonant network switches. Cycle-by-cycle duty cycle control of the PWM waveform effectively performs amplitude modulation of the input voltage and thus controls the output power. The PWM control may also be updated periodically over several PWM cycles, similar to diagram 1202 of FIG. 12 to control average output power control. PWM control method is efficient, simple and can provide fine resolution to power transfer control. Resonant networks used in inverters have a low pass or bandpass filter characteristic such that at resonance there is usually a roll-off in the transfer function. This roll-off can be exploited to control input power by varying drive frequency relative to the resonant frequency of the network. Although this method does provide fine resolution for power control it is difficult to support soft switching and minimize reactive power as the frequency deviates from the nominal operation point. Another frequency control method is the use of subharmonic control. In this method, the input voltage is scaled with a frequency ratio relative to the resonant frequency. Applying the 3rd sub-harmonic frequency, the input voltage gets scaled by ⅓. The main benefit of this method is that the soft switching condition is preserved for all sub-harmonic frequencies. The main drawback is that the voltage can only be scaled by discrete increments (e.g., ⅓, ⅕, ⅐, etc.), similar to diagram 1201 of FIG. 12. The methods described in this paragraph may effectively scale input voltage or power into the resonant network allowing for the removal of the variable DC stage. These methods may be used in combination to produce finer control of the output power.

In circuit (a) of FIG. 9, a series/parallel LC filter is made up of two impedance compensation networks (series LC, and parallel LC). These networks store energy proportional to Q and accomplish only filtering. Better use can be made of these reactive elements by using them for impedance transformation, which will accomplish filtering and some gain. When the inductor and capacitor are arranged in an L-network the network can achieve impedance transformation (resonant gain) and filtering. Particular combinations of these L-networks can achieve transformer like voltage gain, which is relatively insensitive to the load. Circuit (c) of FIG. 9 shows a hybrid topology where some of the gain is achieved by the transformer and some by resonant stage. In circuit (c) of FIG. 9, the filter is a single stage T network, which is also capable of transformer like voltage gain. Gain from single stage networks tend to be limited by practical considerations of avoiding high Q, but a single stage can still achieve significant gains before multi stage networks need to be considered. It is possible to completely eliminate the transformer and strictly use a resonant circuit to achieve all the gain and filtering. This concept is called the resonance transformer. Topologies in circuits (e) and (g) of FIG. 9 accomplish just that. Topology circuits (e) and (g) are multistage and in theory capable of much higher gain without excessively large Q. However the resonant transformer does not provide galvanic isolation which is needed for patient protection. Using a transformer without sacrificing the benefits of the fully resonant transformer is described further. Using construction techniques used in LLC transformers, cases circuits (a) and (c) of FIG. 9 may be converted to the integrated magnetics designs in circuits (b) and (d) of FIG. 9, respectively. Note both of those cases take advantage of the leakage inductance of the transformer. Depending on the value of discrete series inductor it might be absorbed by the transformer without impact to transformer size. Also, because magnetizing inductance Lx is not part of resonant circuit and can remain high, the resulting coupling coefficient k is in the high 0.8-0.9 region allowing use of standard design tools and minimizes concerns of fringing flux. As mentioned before, in circuits (e) and (g) of FIG. 9 galvanic isolation may be desirable for patient use. By inserting a 1:1 transformer and rearranging the resonant circuit inductors it is possible to replicate an equivalent model of a transformer (e.g., see FIG. 10) such that it absorbs two inductors. That is the case in the transition from circuits (e) and (f) of FIG. 9 and from circuits (g) and (h) of FIG. 9. Because inductors in the resonant circuit tend to be close in value it is likely to drive the required coupling coefficient down to the 0.3-0.5 range. This kind of loosely coupled transformer requires unique design approaches and careful attention to fringing flux in regard to nearby components. Typical switching frequencies for ESU generators are 200 KHz to 4 MHz. At such frequencies, the risk of neuromuscular stimulation and electrocution are minimized.

What is claimed is:

1. An electrosurgical generator, comprising: a radio frequency (RF) inverter stage configured to receive a power signal and, in response to control signals, to provide an output signal based on the power signal, wherein the RF inverter stage comprises a resonant isolated transformer circuit configured to receive the power signal and to provide gain and filtering adjustments to the power signal to provide the output signal, wherein the resonant isolated transformer circuit has only one magnetic component, the only one magnetic component being a transformer, wherein the resonant isolated transformer circuit provides multi-stage filtering via the only one magnetic component.

2. The electrosurgical generator of claim 1, wherein the transformer is a loosely coupled transformer having a coupling coefficient less than 1.

3. The electrosurgical generator of claim 2, wherein the coupling coefficient of the loosely coupled transformer less than 0.6.

4. The electrosurgical generator of claim 2, wherein the power signal is an alternating current power signal, wherein the coupling coefficient and inductance values of the loosely coupled transformer are based on direct current signals and harmonics to be filtered from the alternating current power signal.

5. The electrosurgical generator of claim 2, wherein the loosely coupled transformer has a turns ratio of 1:N.

6. The electrosurgical generator of claim 5, wherein the turns ratio of the loosely coupled transformer is 1:1.

7. The electrosurgical generator of claim 1, wherein the resonant isolated transformer circuit has series or parallel capacitance on a primary side and on a secondary side.

8. The electrosurgical generator of claim 1, wherein the resonant isolated transformer circuit can provide at least one of a resistive, a conductive, a transresistive, or a transconductive gain.

9. The electrosurgical generator of claim 8, wherein the resonant isolated transformer circuit provides load independent gain.

10. The electrosurgical generator of claim 1, wherein the power signal is an alternating current power signal, wherein the multi-stage filtering includes circuitry configured to filter direct current signals and harmonics from the alternating current power signal.

11. The electrosurgical generator of claim 1, wherein the resonant isolated transformer circuit is configured to operate in a frequency range between and including 100 kHz and 30 MHz.

12. The electrosurgical generator of claim 1 wherein: the power signal is received without a buck or boost convertor; the transformer has a coupling coefficient less than 1 and a leakage inductance; and the resonant isolated transformer circuit further comprises a plurality of capacitors electrically coupled to the transformer that provide the multi-stage filtering without an additional magnetic component.

13. A method, comprising: receiving an input signal at a resonant stage of a medical device, wherein the resonant stage has only one magnetic component, the only one magnetic component being a resonant isolated transformer; multi-stage filtering, only via the resonant isolated transformer of the resonant stage, the input signal to provide an output signal, and providing the output signal at an output of the medical device.

14. The method of claim 13, further comprising setting a coupling coefficient and inductances of the resonant isolated transformer based on desired filtering of the input signal.

15. The method of claim 13, further comprising setting a coupling coefficient and inductances of the resonant isolated transformer based on desired gain of the input signal.

16. The method of claim 15 wherein the desired gain of the input signal is one of resistive, conductive, transresistive, or transconductive gain, and wherein the desired gain is load independent.

17. The method of claim 13, further comprising setting a coupling coefficient of the resonant isolated transformer to a value less than 0.6.

18. The method of claim 13, where the input signal is a voltage signal.

19. The method of claim 13, where the input signal is a current signal.

20. The method of claim 13, further comprising: providing a current-based signal as the output signal for a first therapy type; and providing a voltage-based signal as the output signal for a second therapy type.

21. The method of claim 13 wherein: the power signal is received without a buck or boost convertor; the resonant isolated transformer has a coupling coefficient less than 1 and a leakage inductance; and the resonant stage further comprises a plurality of capacitors electrically coupled to the resonant isolated transformer such that the multistage filtering is performed without using an additional magnetic component beyond the resonant isolated transformer.

22. An electrosurgical generator, comprising: a radio frequency (RF) inverter stage configured to receive a power signal and, in response to control signals to provide an output signal based on the power signal, wherein the RF inverter stage comprises a resonant isolated transformer circuit configured to receive the power signal and to provide gain and filtering adjustments to the power signal to provide the output signal, wherein the resonant isolated transformer circuit has only one magnetic component, the only one magnetic component being a transformer, wherein the resonant isolated transformer circuit provides multi-stage filtering via the only one magnetic component; the RF inverter stage having a resonant frequency; and a controller coupled to the RF inverter stage and configured to provide the control signals to the RF inverter stage to control the gain and filtering adjustments to the power signal received at the RF inverter stage based on a selected therapy, wherein the controller is configured to drive the RF inverter stage using subharmonic frequencies of the RF inverter stage resonant frequency to control the gain and filtering adjustments to the power signal.

23. The electrosurgical generator of claim 22, wherein the controller further uses duty cycle modulation to control the gain and filtering adjustments to the power signal.

24. The electrosurgical generator of claim 22, wherein the controller comprises a microprocessor and a pulse-width modulation controller.

* * * * *